US00PP33991P2

(12) United States Plant Patent
Kievit et al.

(10) Patent No.: US PP33,991 P2
(45) Date of Patent: Mar. 1, 2022

(54) ***HEUCHERA* PLANT NAMED 'CARNIVAL CINNAMON STICK'**

(50) Latin Name: ***Heuchera* x *hybrida***
Varietal Denomination: Carnival Cinnamon Stick

(71) Applicant: Ball Horticultural Company, West Chicago, IL (US)

(72) Inventors: Christa Kievit, Hem (NL); Karl F. Batschke, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/460,259

(22) Filed: Aug. 29, 2021

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./440
CPC ... A01H 5/02; A01H 5/12; A01H 5/00; A01H 6/80; A01H 1/107; A01H 1/121
See application file for complete search history.

*Primary Examiner* — June Hwu
(74) *Attorney, Agent, or Firm* — Audrey Charles

(57) ABSTRACT

A new and distinct cultivar of *Heuchera* plant named 'Carnival Cinnamon Stick', characterized by its dark reddish-orange and medium green colored foliage, white and reddish-purple colored flowers, and moderately vigorous, mounded growth habit, is disclosed.

2 Drawing Sheets

Latin name of genus and species of plant claimed: *Heuchera* x *hybrida*.
Variety denomination: 'Carnival Cinnamon Stick'.

BACKGROUND OF THE INVENTION

The present invention relates to a new and distinct cultivar of *Heuchera* plant botanically known as *Heuchera* x *hybrida* and hereinafter referred to by the cultivar name 'Carnival Cinnamon Stick'.

The new cultivar originated in a controlled breeding program in Hem, The Netherlands during the summer of 2016. The objective of the breeding program was the development of *Heuchera* cultivars with heat tolerance, unique foliage coloration and a mounded growth habit.

The new *Heuchera* cultivar is the result of open-pollination. The female (seed) parent of the new cultivar is 'Carnival Watermelon', U.S. Plant Pat. No. 24,803, characterized by its immature foliage color of greyed burgundy-red with a slight silvery overlay and prominent reddish to reddish-brown venation, mature foliage color of greyed-green and prominent green venation, and moderately vigorous and mounded growth habit. The male (pollen) parent of the new cultivar is unknown. The new cultivar was selected as a single flowering plant within the progeny of the above stated open-pollination during July 2017 in a controlled environment in Hem, The Netherlands.

Asexual reproduction of the new cultivar by in vitro propagation since July 2017 in Tenjo, Colombia and Bremen, Germany has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Carnival Cinnamon Stick' as a new and distinct cultivar of *Heuchera* plant:

1. Dark reddish-orange and medium green colored foliage;
2. White and reddish-purple colored flowers; and
3. Moderately vigorous, mounded growth habit.

Plants of the new cultivar differ from plants of the female parent primarily in having less prominent venation and darker reddish orange with no silvery overlay.

Of the many commercially available *Heuchera* cultivars, the most similar in comparison to the new cultivar is 'Carnival Peach Parfait', U.S. Plant Pat. No. 24,928. However, in comparison, plants of the new cultivar differ from plants of 'Carnival Peach Parfait' in at least the following characteristics:

1. Plants of the new cultivar have a foliage color that is darker reddish-orange colored than plants of 'Carnival Peach Parfait';
2. Plants of the new cultivar have a foliage margin that is less wavy than plants of 'Carnival Peach Parfait'; and
3. Plants of the new cultivar have a flower color that has more reddish-purple colored calyx and petals than plants of 'Carnival Peach Parfait'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Carnival Cinnamon Stick'. The plants were approximately nine-months old. The plants were grown for approximately 15 weeks in an outdoor garden-type bed or three-quart containers in an outdoor shade nursery in West Chicago, Ill.

DETAILED BOTANICAL DESCRIPTION

Figure 1:
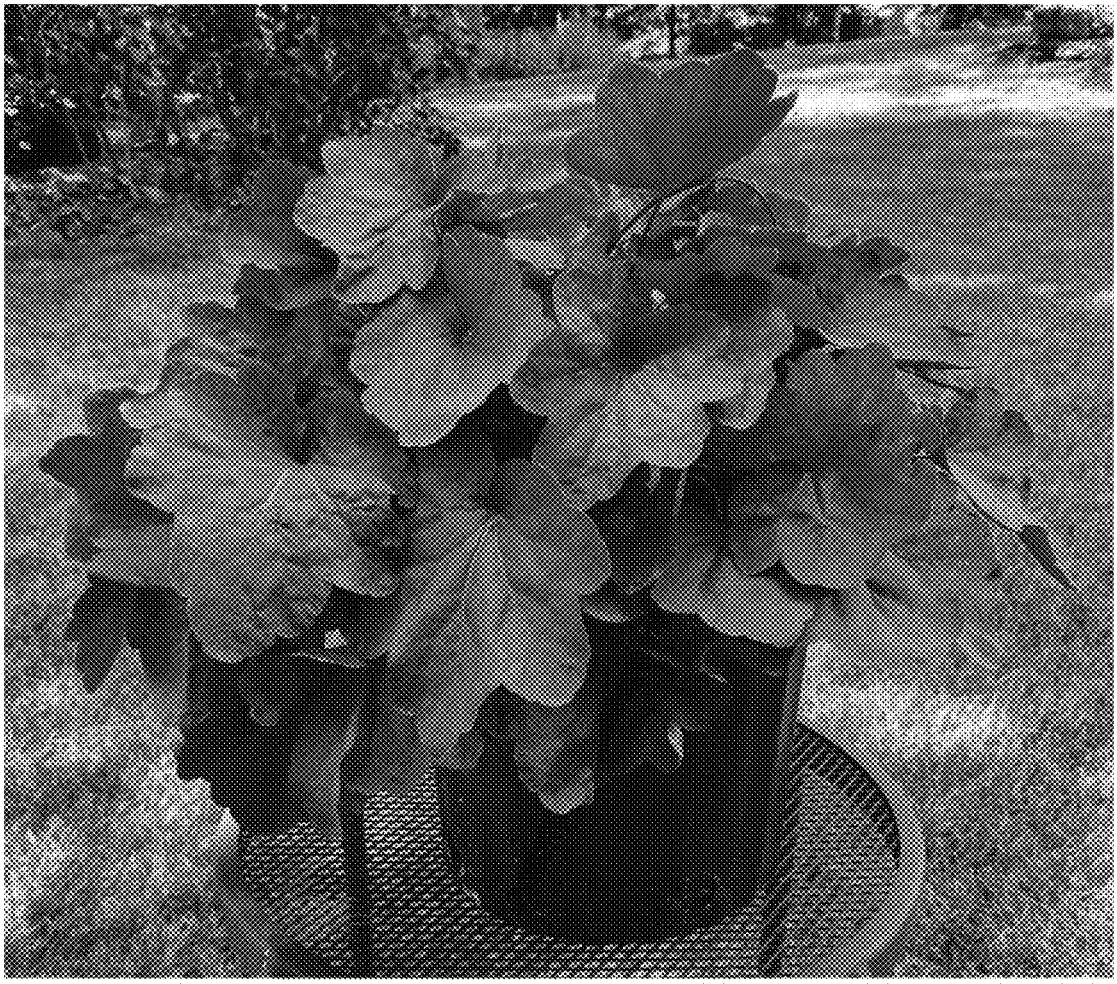
FIG. 1 illustrates a side view of the overall growth habit of 'Carnival Cinnamon Stick'.
Figure 2:
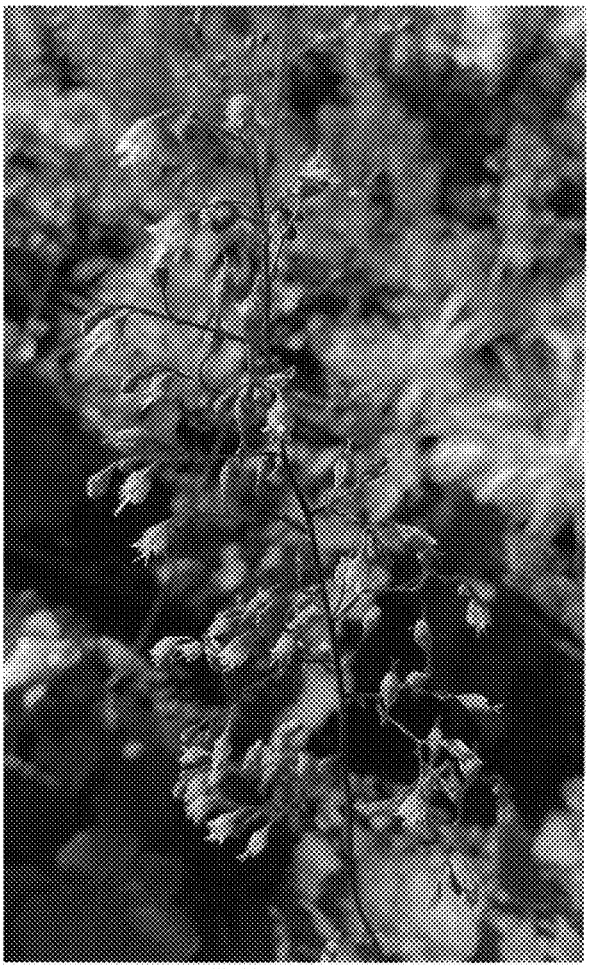
FIG. 2 illustrates a close-up view of an individual inflorescence of 'Carnival Cinnamon Stick'.
Figure 3:
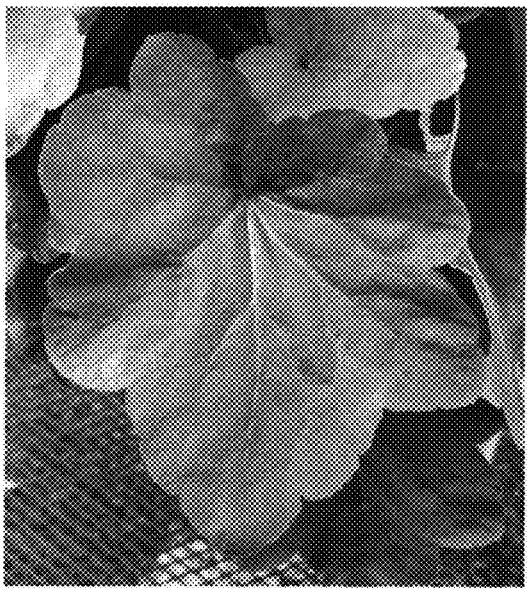
FIG. 3 illustrates a close-up view of an individual leaf of 'Carnival Cinnamon Stick'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2021 under natural light conditions in Naperville, Ill.

The following descriptions and measurements describe approximately nine-month-old plants produced from in vitro plantlets and grown under conditions comparable to those used in commercial practice. The plants were grown in 1.7-gallon containers for approximately 15 weeks in an outdoor shade nursery in West Chicago, Ill. Inflorescence data was collected from plants of the same age transplanted into an outdoor garden-type shade nursery bed in West Chicago. Prior to transplant plants were grown in liners in a poly-covered greenhouse in West Chicago, Ill. Greenhouse temperatures ranged from an average high of 79.5° F. (26.4° C.) to an average low of 68.5° F. (20.3° C.), and supplemental lighting was provided daily for five hours during short days. Measurements and numerical values represent averages of typical plants.

Botanical classification: *Heuchera* x *hybrida* 'Carnival Cinnamon Stick'.

Parentage:

*Female parent*.—'Carnival Watermelon', U.S. Plant Pat. No. 24,803.

*Male parent*.—Unknown.

Propagation:

*Type*.—In vitro propagation is preferred, divisions are possible.

*Time to initiate roots in vitro*.—Approximately 10 days at 20° C.

*Time to produce a rooted plantlet in summer*.—Approximately 42 days.

*Root description*.—Fine, fibrous.

*Rooting habit*.—Freely branching.

Plant description:

*Commercial crop time*.—Approximately 6 to 8 weeks from a rooted tissue culture plantlet to finish in a 10 cm container.

*Growth habit and general appearance*.—Clump-forming herbaceous perennial, mounded foliage.

*Growth rate*.—Moderately vigorous.

*Hardiness*.—USDA Zone 4a (−30° F. to −25° F./−34.4° C. to −31.7° C.).

*Size*.—Height from soil level to top of foliage: Approximately 20.0 cm. Width: Approximately 54.0 cm.

*Branching habit*.—No branching, basal rosettes of leaves on petioles. Number of rosettes per plant: Approximately 8.

Foliage description:

*General description*.—Moderately durable to environmental stresses. Quantity of leaves per rosette: Approximately 12. Fragrance: None. Form: Simple. Arrangement: Alternate to whorled. Density: Dense.

*Leaves*.—Aspect: Blade is at an acute angle to nearly perpendicular to petiole. Shape: Orbicular. Margin: Crenate with few and very shallow indentations, moderately lobed, slightly wavy, ciliate. Apex: Minutely apiculate. Base: Cordate, sometimes slightly overlapping. Venation pattern: Palmate. Length of mature leaf: Approximately 12.0 cm. Width of mature leaf: Approximately 12.5 cm. Texture of upper surface: Dull, very weak rugosity, sparsely pubescent with short hairs. Texture of lower surface: Slightly glossy, sparsely pubescent with short hairs. Color of upper surface of young foliage: Closest to 178A to 178B with base of main veins of 182B. Color of lower surface of young foliage: Closest to but lighter than N186D with base of main veins of 182C. Color of upper surface of mature foliage: Closest to 178A to 178B with 146A to 146B, base of main veins of 182C, the dark reddish-orange coloration fades during the fall season and the leaves become predominately 146A to 146B with base of main veins of 182C. Color of lower surface of mature foliage: Closest to but lighter than N186D with base of main veins of 155C, transitioning during the fall season to closest to but lighter than N186D with N187C and base of main veins of 155C.

*Petiole*.—Length: Approximately 19.5 cm. Diameter: Approximately 3.0 mm. Texture: Sparsely pubescent. Color: 147D with an overlay of N186D, overlay is heavier on younger petioles.

*Stipules*.—Two leafy stipules located at the base of petioles. Apex: Acute. Length: Approximately 7.0 mm. Width: Approximately 3.0 mm. Color: Closest to N186D.

Flowering description:

*Flowering habit*.—'Carnival Cinnamon Stick' flowers once a year during late spring to midsummer under outdoor conditions.

*Lastingness of individual flower on the plant*.—Approximately 7 days.

Inflorescence description:

*General description*.—Type: Compound spike emerging from the base of the rosette with two to three cauline leaves. Density: Sparse. Fragrance: None. Length or height excluding the peduncle: Approximately 31.5 cm. Width: Approximately 10.0 cm. Quantity of inflorescences per plant: Approximately 4. Quantity of flowers per inflorescence: Approximately 80.

*Peduncle*.—Strength: Moderate. Aspect: Erect to approximately 30° angle from vertical. Length: Approximately 29.0 cm. Diameter at midpoint: Approximately 3.0 mm. Texture: Densely pubescent. Color: 187A.

Flower description:

*General description*.—Type: Single, campanulate, self-cleaning. Aspect: Drooping to slightly outward.

*Bud*.—Rate of opening: Generally takes 4 days for bud to progress from first color to fully open flower.

*Bud just before opening*.—Shape: Broadly obovate. Length: Approximately 4.0 mm. Diameter: Approximately 3.0 mm. Texture: Densely pubescent with a mixture of glandular and nonglandular hairs. Gland Color: 79A. Color: 187C with upper third of 70A.

*Corolla*.—Shape: Campanulate. Diameter: Approximately 5.0 mm. Depth: Approximately 7.0 mm.

*Petals*.—Quantity: 5. Arrangement: Single whorl. Shape: Narrowly elliptic. Appearance: Dull. Margin: Entire. Apex: Acute. Base: Lower half fused into hypanthium. Length: Approximately 7.0 mm. Width: Approximately 1.0 mm. Texture of upper and lower surfaces: Moderately glandular pubescent. Gland color: 79B. Color of upper and lower surfaces when first and fully open: NN155D with a faint longitudinal streak of 70B.

*Calyx*.—Shape: Campanulate. Diameter: Approximately 5.0 mm. Depth: Approximately 7.0 mm.

*Sepals*.—Quantity per flower: 5. Shape: Elliptic. Appearance: Dull. Margin of free portion: Entire. Apex: Acute. Base: Lower half fused into hypanthium. Length: Approximately 7.0 mm. Width at rim of hypanthium: Approximately 3.0 mm. Texture of upper and lower surfaces: Densely pubescent with a mixture of glandular and nonglandular hairs. Gland Color: 79B. Color of upper surface: NN155D tinted with 70B. Color of lower surface: NN155D with an overlay of 187C on lower half and 70B on upper half.

*Pedicel*.—Strength: Moderate. Aspect: The pedicel of the central flower of each spikelet is directly on top of the secondary pedicel, pedicels of secondary and tertiary flowers of each spikelet have an average 40° angle from vertical. Length: Approximately 3.0 mm. Diameter: Less than 1.0 mm. Texture: Densely pubescent with a mixture of glandular and nonglandular hairs. Gland color: N186A. Color: 187A.

*Reproductive organs*.—Androecium: Quantity: 5 per flower. Anther shape: Bilobed, ovoid. Anther length: Less than 1.0 mm. Anther color: 24B. Filament length: Approximately 3.0 mm. Filament color: NN155D. Pollen amount: Abundant. Pollen color: 24A. Gynoecium: Pistil quantity: 2 per flower. Pistil length: Approximately 8.0 mm. Stigma shape: Pointed. Stigma color: NN155D. Style length: Approximately 6.0 mm. Style color: NN155D, opaque. Ovary color: NN155C with 160A at base.

Seed and fruit production: Neither seed nor fruit production has been observed.

Disease and pest resistance: Resistance to pathogens and pests common to *Heuchera* has not been observed.

What is claimed is:

1. A new and distinct cultivar of *Heuchera* plant named 'Carnival Cinnamon Stick', substantially as herein illustrated and described.

* * * * *